(12) United States Patent
Wöldike et al.

(10) Patent No.: US 8,535,909 B2
(45) Date of Patent: Sep. 17, 2013

(54) E. COLI BL21 STRAIN LACKING A FUNCTIONAL GROUP II CAPSULAR GENE CLUSTER

(75) Inventors: Helle Fabricius Wöldike, Måløv (DK); Jianhui Deng, Beijing (CN); Xin Zhao, Beijing (CN); Yun Liu, Beijing (CN); Jing Su, Beijing (CN)

(73) Assignee: Novo Nordisk A/S, Bagsvaerd (DK)

( * ) Notice: Subject to any disclaimer, the term of this patent is extended or adjusted under 35 U.S.C. 154(b) by 84 days.

(21) Appl. No.: 13/126,379

(22) PCT Filed: Nov. 10, 2009

(86) PCT No.: PCT/EP2009/064903
§ 371 (c)(1),
(2), (4) Date: May 31, 2011

(87) PCT Pub. No.: WO2010/052335
PCT Pub. Date: May 14, 2010

(65) Prior Publication Data
US 2011/0236929 A1      Sep. 29, 2011

Related U.S. Application Data

(60) Provisional application No. 61/115,122, filed on Nov. 17, 2008.

(30) Foreign Application Priority Data

Nov. 10, 2008  (EP) .................................... 08168750

(51) Int. Cl.
C12P 21/06    (2006.01)
C12N 1/20     (2006.01)

(52) U.S. Cl.
USPC ..................................... 435/69.1; 435/252.33

(58) Field of Classification Search
USPC .......................................... 435/252.33, 69.1
See application file for complete search history.

(56) References Cited

FOREIGN PATENT DOCUMENTS
WO    WO 97/49416    12/1997
WO    WO 02/14468    2/2002

OTHER PUBLICATIONS

Andreishcheva et al., "*Escherichia coli* BL21 (DE3) Chromosome Contains a Group II Capsular Gene Cluster," Gene, 2006, vol. 384, pp. 113-119.
Muhldorfer I et al., "Genetic Aspects of *Escherichia coli* Virulence," Academic Press, 1994, vol. 16, pp. 171-181.
Datsenko Kirill A et al., "One-Step Inactivation of Chromosomal Genes in *Escherichia coli* K-12 Using PCR Products," Proc Natl Acad Sci U S A, 2000, vol. 12, pp. 6640-6645.
Lopes D H J et al, "Amyloidogenicity and Cytotoxicity of Recombinant Mature Human Islet Amyloid Polypeptide (rhIAPP)," Biol Chem, 2004, vol. 279, No. 41, pp. 42803-42810.
Cross A S et al. "The Importance of the KL Capsule in Invasive Infections Caused by *Escherichia coli*" The Journal of Infectious Diseases 1984 vol. 149(2) 184-193.
Elena S F et al. "Genomic Divergence of *Escherichia coli* Strains: Evidence for Horizontal Transfer and Variation in Mutation Rates" International Microbiology 2005 vol. 8 pp. 271-278.
Whitfeld C et al. "Structure, Assembly and Regulation of Expression of Capsules in *Escherichia coli*" Molecular Microbiology 1999 vol. 31 (5) pp. 1307-1319.
Jann K et al. "Capsules of *Eschericia coli*, Expression and Biological Significance" Canadian Journal of Microbiology 1992 vol. 38 pp. 705-710.
M.M. Roberts I et al. "Molecular Cloning and Analysis of Genes for Production of K5, K7, K12 and K92 Capsular Polysaccharides in *Escherichia coli*" Journal of Bacteriology. 1986 vol. 168(3) pp. 1228-1233.
Roberts JA. "Tropism in Bacterial Infections: Urinary Tract Infection" The Journal of Urology. 1996 vol. 156 pp. 1552-1559.
M.M. Orskov Frits et al. "*Escherichia coli* Serotyping and Disease in Man and Animals" Candian Journal of Microbiology. 1992 vol. 38. pp. 699-704.
Taylor CM et al. "Capsular Polysaccharides and Their Role in Virulence" Contributions to Microbiology. 2005 vol. 12 pp. 55-66.
Vimr R E et al. "Genetic Analysis of Chromosomal Mutations in the Polysialic Acid" Journal of Bacteriology. 1989 vol. 171(2) pp. 1106-1117.

*Primary Examiner* — Maryam Monshipouri
(74) *Attorney, Agent, or Firm* — Jianjie Hu

(57) ABSTRACT

The present invention relates to a novel non-pathogenic *Escherichia coli* (*E. coli*) B BL21 strain comprising a deletion of group II capsular gene cluster, and the use thereof for the production of peptides.

14 Claims, 7 Drawing Sheets a)

b)

E. COLI BL21 STRAIN LACKING A FUNCTIONAL GROUP II CAPSULAR GENE CLUSTER

CROSS-REFERENCE TO RELATED APPLICATIONS

This application is a 35 U.S.C. §371 national stage application of International Patent Application PCT/EP2009/064903 (published as WO 2010/052335), filed Nov. 10, 2009, which claimed priority of European Patent Application 08168750.1, filed Nov. 10, 2008; this application further claims priority under 35 U.S.C. §119 of U.S. Provisional Application 61/115,122, filed Nov. 17, 2008.

FIELD OF THE INVENTION

The present invention relates to the manipulation of Escherichia coli (E. coli) genome, to an improved non-pathogenic E. coli B strain, and its use thereof for the production of peptides and proteins.

INCORPORATION-BY-REFERENCE OF THE SEQUENCE LISTING

In accordance with 37 C.F.R. §1.52(e)(5), Applicants enclose herewith the Sequence Listing for the above-captioned application entitled "SEQUENCE LISTING", created on Apr. 26, 2011. The Sequence Listing is made up of 12 kilobytes, and the information contained in the attached "SEQUENCE LISTING" is identical to the information in the specification as originally filed. No new matter is added.

BACKGROUND OF THE INVENTION

Bacteria have been used to produce a wide range of commercial products. The use of genetically engineered bacteria like E. coli as host cells for the production of biological reagents such as peptides and nucleic acids in the laboratory and industry, is well-known in the art. Bacteria in their natural environment are exposed to many conditions that are not normally experienced in standard industrial or laboratory growth, and thus their genomes carry a large number of condition-dependent, stress-induced genes or otherwise non-essential genes which may not be needed in industrial or laboratory use of the organisms, or may even be unwanted.

Bacterial pathogens contain virulence factors such as capsular polysaccharides at the cell surface, which mediate the interactions between the bacterium and its immediate environment and have a number of functions directly related to their pathogenicity. More than 80 serologically and chemically distinct types of polysaccharide capsules have been described in E. coli and termed K antigens. The polysaccharide capsules have been classified into 4 groups, of which the group II capsular polysaccharides are similar to those of Haemophilus influenzae and Neisseria meningitides. The group II capsular gene clusters contain most of the capsular types associated with invasive disease and have a conserved genetic organisation consisting of three functional regions. Regions 1 and 3 are conserved among group II gene clusters and encode peptides necessary for the transport of the polysaccharide from its site of synthesis to the cell surface, while region 2 is serotype specific and encodes the enzymes responsible for biosynthesis and polymerization of the individual monosaccharides that comprise the particular polysaccharide. Region 1 comprises 6 genes kpsFEDUCS, organised in a single transcriptional unit. Region 2 is serotype specific and differs among group 2 antigens. Region 3 contains 2 genes kpsM and kpsT organised in a single transcriptional unit [Andreishcheva et al. Gene (2006) 384: 113-119].

The E. coli strains K-12 and B are not encapsulated and are commonly used strains for the production of peptides. The E. coli K-12 genome has been fully sequenced and does not contain any capsular genes. It has been found that E. coli B BL21(DE3), which is a preferred strain for high-yield expression of recombinant peptides, contains a cluster of genes coding for group II capsular polysaccharides and it is thought that an ancestor of E. coli B must have acquired these capsular genes by horizontal transfer. The K antigens located in the capsule of E. coli are often associated with a pathogenic phenotype in strains harbouring the functional form of the genes. It has been shown that in E. coli B BL21, the region 2 of group II capsular gene cluster has become inactive by an insertion element (IS1), preventing the production of the antigen, while region 1 and 3 supporting export and presentation of wildtype capsular antigen, are still intact [Andreishcheva et al. Gene (2006) 384: 113-119]. However, there is a theoretical possibility of re-establishing a functional group II capsular gene cluster, e.g. if the IS1 in region 2 is lost and thereby the group II cluster may be re-established. Alternatively, if the IS1 mutated region is exchanged by an exogenous wildtype region 2, the group II cluster may also be re-established.

The present invention provides an E. coli B BL21 (DE3) strain with permanent knock out (KO) of the group II capsular gene cluster, bringing this strain into the same safety class as other commercially important strains such as E. coli K-12.

SUMMARY OF THE INVENTION

The present invention relates to an E. coli B BL21 strain having an irreversibility inactivated group II capsular gene cluster.

In one embodiment E. coli B BL21 strain is characterised by having a total or partial deletion of the group II capsular gene cluster.

In one embodiment E. coli B BL21 strain is characterised by having total deletion of the group II capsular gene cluster.

In one embodiment E. coli B BL21 strain is characterised by having a partial deletion of the group II capsular gene cluster.

In a further embodiment, the E. coli B BL21 strain is characterised by having one or more point mutations in the group II capsular gene cluster.

In another embodiment, the E. coli strain is characterised by having at least 5% of group II capsular gene cluster permanently inactivated by deletion.

In another embodiment, the E. coli strain is characterised by having at least 25% of group II capsular gene cluster permanently inactivated by deletion.

In another embodiment, the E. coli strain is characterised by having at least 40% of group II capsular gene cluster permanently inactivated by deletion.

In another embodiment, the E. coli strain is characterised by having at least 55% of group II capsular gene cluster permanently inactivated by deletion.

In another embodiment, the E. coli strain is characterised by having from 75% to 100% of the group II capsular gene cluster permanently inactivated by deletion.

In another embodiment, the E. coli strain is characterised by having at least 85% of group II capsular gene cluster permanently inactivated by deletion.

In another embodiment, the E. coli strain is characterised by having at least 95% of group II capsular gene cluster permanently inactivated by deletion.

In one embodiment, 30% of the group II capsular gene cluster is deleted.

In another embodiment, 50% of the group II capsular gene cluster is deleted.

In another embodiment, 70% of the group II capsular gene cluster is deleted.

In another embodiment, 80% of the group II capsular gene cluster is deleted.

In another embodiment, 90% of the group II capsular gene cluster is deleted.

In one embodiment, the *E. coli* strain is *E. coli* B BL21 (DE3) and in a further embodiment the *E. coli* strain is *E. coli* B BL21(DE3)ΔdadX Δalr.

The present invention also contemplates a method for producing an *E. coli* B strain wherein the group II capsular gene cluster is deleted by a method comprising the steps of:
 a. replacing of group II capsular gene cluster by a selection marker,
 b. eliminating the selection marker and
 c. confirming the deletion by PCR analysis.

In one embodiment, the selection marker is an antibiotic resistance gene.

In another embodiment, the antibiotic resistance gene is selected from the group consisting of chloramphenicol, tetracyclin, ampicillin, kanamycin, vancomycin and erythromycin.

In yet another embodiment, the antibiotic resistance gene is chloramphenicol.

The invention is also related to a method for producing a peptide by introducing an expression vector comprising a DNA sequence encoding a peptide in the *E. coli* strain of the present invention.

In one embodiment the present invention also contemplates a method for the production of a peptide comprising culturing an *E. coli* B strain according to the present invention, in a suitable culture medium under condition for the expression of DNA encoding the said peptide. The peptide to be expressed by the expression vector may be any peptide which can be expressed in *E. coli*. Representative examples of such peptides are hGH, glucagon-like peptides, interleukins, insulin analogues, wildtype adiponectin, FGF-21, trypsin, aprotinin, amylin and leptin and analogs thereof, as well as enzymes such as sialidase, transglutaminase (tGase), HRV (Human Rhino Virus) 3C protease, Tobacco Etch Virus (TEV) protease and variants thereof.

In one embodiment, the *E. coli* strain of the present invention comprises an expression vector comprising a DNA sequence encoding a peptide.

In one embodiment, the peptide to be produced is hGH.

In another embodiment, the peptide to be produced is FGF-21.

In another embodiment, the peptide to be produced is amylin.

In another embodiment, the peptide to be produced is leptin.

In another embodiment, the peptide to be produced is sialidase.

DESCRIPTION OF THE INVENTION

The present invention relates to an *E. coli* B BL21 strain with an irreversibly inactivated group II cluster providing a permanently safe strain for the production of peptides.

The impairment or inactivation of the group II capsular gene cluster of the wildtype or any other strain of *E. coli* B BL21(DE3) may be accomplished by any suitable technique including deletion of the whole cluster or a part thereof or by one or more point mutations in the gene cluster.

The *E. coli* strain of the present invention has the advantage of providing a more robust and high yielding process for production of peptides, compared to commonly industrially used strains, such as *E. coli* K-12.

The *E. coli* B BL21(DE3) used in the present invention may be a double knockout (2xKO) as described in WO2008/025744. This *E. coli* B BL21(DE3) strain has a deletion of 2 genes alr and dadX which both code for D,L-alanine racemase. This double knock out strain cannot grow without either the addition to the growth medium of D-alanine or without the presence of one of the racemase genes on a plasmid, which can supply the necessary D-alanine. This 2xKO D-alanine auxotrophic *E. coli* strain, referred to herein as *E. coli* B BL21(DE3)ΔalrΔdadX, enables a non-antibiotic selection procedure for maintenance of plasmids in the cells.

In one embodiment of the present invention, one or more genes within the group II capsular gene cluster of the wildtype *E. coli* B BL21(DE3) or *E. coli* B BL21(DE3)ΔalrΔdadX strain are deleted. The *E. coli* strain B BL21 (DE3) is described by Studier and Moffat, [J. Mol. Biol. (1986) 189: 113-130] and Studier et al. [Methods in Enzymology (1990) 185:60-89] and is available from Stratagene and Novagen.

In one embodiment of the present invention, one or more genes within the group II capsular gene cluster of the wildtype *E. coli* B BL21(DE3) are deleted. In another embodiment of the present invention, one or more genes within the group II capsular gene cluster of *E. coli* B BL21(DE3)ΔalrΔdadX are deleted.

Figure 1:
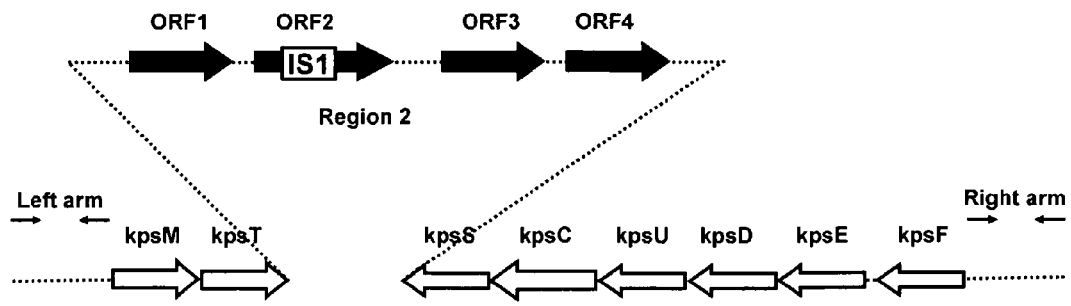
FIG. 1. shows the genetic organisation of the *E. coli* B BL21(DE3) capsular gene cluster with non-coding flanking regions. Open reading frames (ORFs) of the B BL21(DE3) capsular gene cluster (large arrows); direction of transcription (arrowheads): region 1 genes (grey arrows); region 2 ORFs (black arrows); region 3 genes (white arrows); IS1 element (white box). [Andreishcheva et al. Gene (2006) 384: 113-119]. Small arrows indicate the position of the non-coding left arm (LA) and the right arm (RA).

In another embodiment, the gene or genes of choice for deletion within the group II capsular gene cluster are those responsible for potential pathogenecity. Deletion of the entire 16 kb group II capsular gene cluster provides the prevention of the potential re-establishment of the pathogenic capsular phenotype. FIG. 1 shows the genes involved in group II capsular gene cluster of capsular strains including region 1 genes kpsFEDUCS, region 2 ORF1-4 and region 3 kpsM and kpsT. Any one of these genes or combinations thereof may be deleted.

The total deletion of the group II capsular gene cluster, means deletion of the 3 regions, ie., Δ (kpsM-kpsF). The *E. coli* B strains obtained are *E. coli* B BL21(DE3) Δ (kpsM-kpsF) and *E. coli* B BL21(DE3)ΔalrΔdadX Δ (kpsM-kpsF).

In one embodiment, the present invention contemplates any modification sufficient to inactivate the group II gene cluster, apart from the insertion element (IS1).

Bacteria are haploid organisms, i.e. they have only one chromosome, so recombination usually occurs only when new DNA is picked up from the environment, for example, through transformation. Furthermore, bacteria are not readily transformable with linear DNA, e.g., because of intracellular exonucleases that degrade linear DNA. However, recombination-proficient mutants lacking exonucleases of the recombination complex, are transformable with linear DNA. Recombinases are enzymes that catalyze natural recombination reactions and it has been shown that the λ Red shows an enhanced recombination rate when compared with other recombination systems. The method for deletion of the group II capsular gene cluster of the strain of the present invention may be based on the Red-mediated recombination technology developed by Datsenko and Wanner [(2000) PNAS 97(12): 6640-6645] or other conventional methodologies.

Figure 2:
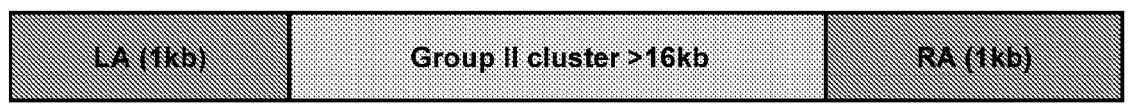
FIG. 2. is a schematic representation of the workflow of the group II capsular gene cluster knock out method: a) replacement of group II capsular gene cluster by an antibiotic resistance gene and b) elimination of the antibiotic resistance gene.
Figure 2:
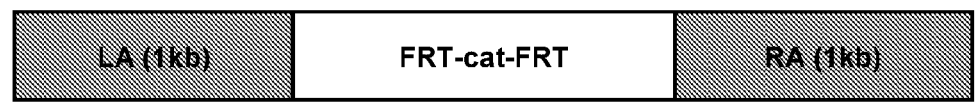
Figure 2:

FIG. 2 shows a schematic view of how to delete the 16 kb group II capsular gene cluster of a strain of the present invention. In one embodiment, the first step in the method is the replacement of the 16 kb group II capsular gene cluster with a selection marker that is generated by PCR by using primers with nucleotide homology extensions or regions, RA and LA (see FIG. 1). This is accomplished by Red-mediated recombination in these flanking homology extensions. After selection, the second step in this method is the elimination of the selection marker by using a helper plasmid expressing the FLP recombinase, which acts on the directly repeated FRT (FLP recognition target) sites flanking the selection marker. The Red and FLP helper plasmids are cured by growth at 37° C., since they are temperature sensitive replicons. The third step includes the confirmation of the deletion by PCR analysis.

Bacterial transformation may be referred to as a stable genetic change brought about by taking up DNA and competence refers to the state of being able to take up exogenous DNA. Some bacteria are naturally capable of taking up DNA under laboratory conditions and such species carry sets of genes specifying machinery for bringing DNA across the cell's membrane or membranes, while others have to be induced by laboratory procedures in which cells are passively made permeable to DNA, using conditions that do not normally occur in nature. Chilling cells in the presence of divalent cations such as $Ca^{2+}$ (in $CaCl_2$) prepares the cell walls to become permeable to plasmid DNA. Cells are incubated on ice with the DNA and then briefly heat shocked (e.g. 42° C. for 30-120 seconds), which causes the DNA to enter the cell and is a well-known method in the art [Sambrook et al., A Laboratory Manual (1989) CSH]. Electroporation is another way to make holes in bacterial (and other) cells, by briefly shocking them with an electric field in the kV range. Plasmid DNA can enter the cell through these holes. This method is amenable to use with large plasmid DNA. Natural membrane-repair mechanisms will rapidly close these holes after the shock. In order to persist and be stably maintained in the cell, a plasmid DNA molecule must contain an origin of replication, which allows it to be replicated in the cell independently of the chromosome.

When employing any of the gene inactivation methodologies described herein, any targeted inactivation of part or the whole group II gene cluster is detected by a selection marker so that the modified *E. coli* B BL21 strain clone can be identified and isolated.

The selection marker may be any suitable marker gene such as an antibiotic resistance gene or an auxotrophic marker.

Suitable antibiotic resistance genes are chloramphenicol, tetracyclin, ampicillin, kanamycin, vancomycin and erythromycin or any other representatives of the β-lecterns, the aminoglycosides, the glycopeptides or the macrolide antibiotics.

The term "cloning" as used herein entails making multiple identical copies of a sequence of DNA. The target DNA sequence is then inserted into a cloning vector. Because this vector originates from a self-replicating virus, plasmid, or higher organism cell when the appropriate size DNA is inserted the "target and vector DNA fragments are then ligated" and create a recombinant DNA molecule. The recombinant DNA molecules are then put into a bacteria strain (usually *E. coli*) which produces several identical copies after transformation. Transformation is the DNA uptake mechanism possessed by bacteria. However, only one recombinant DNA molecule with a given replication origin can be established within a single bacteria cell, so each clone harbors just one DNA insert.

The terms "genome" or "genetic composition" as used herein refer to the entire genetic matter, both structural and functional, which is inheritable and/or otherwise transferable, and is contained within an identified cell or microorganism. The genome (genetic composition) of a microorganism is thus understood to include both chromosomal DNA and extrachromosomal DNA (e.g. plasmids, R factors and the like).

The term "about" as used herein means in reasonable vicinity of the stated numerical value, such as plus or minus 10%.

The term "knockout" as used herein, means a genetically engineered bacteria strain in which one or more genes have been deleted or inactivated (have been "knocked out" of the organism). Knockout organisms are normally used as models for studying the role of genes which have been sequenced but have unknown functions. Knockout techniques may be used to remove undesired and/or potentially pathogenic genes from organisms of interest.

The term "gene cluster" as used herein means a set of two or more genes which are genetically and functionally coupled. Because populations from a common ancestor tend to possess varieties of the same gene clusters, they are useful for tracing back recent evolutionary history.

The term "parental strain" may be any bacterial strain from which the reduced genome strain is derived. Representative examples of parent strains according to the present invention include, but are not limited to, *E. coli* strains such as B or C, or a strain with a genome sequence substantially identical thereto.

The terms "level" or "amount" of peptide produced in a given bacterial host cell, as used herein may refer to a quantitative measure of peptide present or detectable, in accordance with the method of production selected, in the cell culture. For example, if the method of peptide production chosen results in an accumulation of peptide within the cell itself, then the level or amount of peptide produced will be that quantitative measure of peptide present with the cells themselves. If the method of peptide production involves secretion of the peptide, then the level of peptide production will be that quantitative measure of peptide present in the growth medium.

The term "yield" of peptide, as used herein refers to a quantitative amount of an essentially pure peptide, which peptide is retrieved and/or purified essentially free from peptides naturally associated with the host strain. In ascertaining a quantitative "yield" or "amount" of peptide produced by a bacterial host cell, such as *E. coli* B BL21 strains, conventional peptide-specific methods such as immunoassay, high performance liquid chromatography (HPLC), enzymatic activity, spectrophotometric techniques, SDS-PAGE and the like can be employed.

The term "expression control sequence" used herein means a promoter or array of transcription factor binding sites that direct transcription of a nucleic acid operatively linked thereto.

The term "free end" used in reference to a double-stranded nucleic acid may mean a linear nucleic acid with blunt free ends or sticky free ends, or a combination thereof.

The term "gene" used herein refers to a nucleic acid (e.g., DNA or RNA) that comprises a nucleic acid sequence encoding a polypeptide or precursor thereto. The polypeptide can be encoded by a full length coding sequence or by any portion of the coding sequence so long as the desired activity or functional properties (e.g., enzymatic activity, ligand binding, signal transduction, antigenicity etc.) of the full-length or fragment are retained. The term also encompasses the sequences located adjacent to the coding region on both the 5' and 3' ends that contribute to the gene being transcribed into a full-length mRNA. The term "gene" encompasses both cDNA and genomic forms of a gene. A genomic form or clone of a gene may contain the coding region interrupted with non-coding sequences termed (e.g., introns).

The terms "introduce" or "introduced", when used in reference to adding a nucleic acid to a strain, means that the nucleic acid may be integrated into the chromosome of the strain or contained on a vector, such as a plasmid, in the strain.

The terms "open reading frame" or "ORF" as used herein refers to a genetic sequence that does not contain stop codons.

The terms "peptide", "polypeptide" or "protein" are used interchangeably herein and mean a peptide, polypeptide and protein, whether native or recombinant, as well as fragments, derivatives, homologues, variants and fusions thereof.

The growth of group II knock out strains was evaluated in shake flasks and in high density fermentors and compared with their parental strains. The experiments showed that group II knock out does not affect the growth of the cells in either strain background. Expression vector harbouring several peptides were transformed into group II deleted strains for expression tests in a high density fermentor.

In one embodiment, the peptides for production in the *E. coli* B strains of the present invention may be selected from the group consisting of, but not limited to hGH, glucagon-like peptides, interleukins, insulin analogs, wildtype adiponectin, FGF-21, trypsin, aprotinin, amylin and leptin and analogs thereof. Enzymes such as sialidase, transglutaminase (tGase), HRV (Human Rhino Virus) 3C protease, Tobacco Etch Virus (TEV) protease and variants thereof, and any other peptide or peptide for which an expression system is operable in *E. coli*.

The present invention also relates to a method of preparing human peptides as mentioned above. In general, a cloned wildtype peptide nucleic acid sequence is modified to encode the desired protein. This modified sequence is then inserted into an expression vector, which is in turn transformed or transfected into host cells. Operable expression systems typically include the conventional gene expression components set forth by Studier and Moffat [J. Mol. Biol. (1986) 189:113-130] and Studier et al. [Methods in Enzymology (1990) 185: 60-89].

The peptides to be produced in the host cells can be synthesized as fusion peptides, secreted into the media or into the periplasmic space, produced in free form in the cytoplasm, or accumulated in intracellular bodies such as in inclusion bodies. Purification of the peptides similarly involves the use of aforementioned conventional, publicly available methodologies which are adapted, again by conventional techniques, to the peptide of interest.

The present invention is suitable for the production of any type of peptide.

In one embodiment, the peptide selected for production in the group II knock out E. coli/B BL21 host cells is human growth hormone (hGH) and in one embodiment the human growth hormone (hGH) is produced from a precursor peptide as described in EP217814, which describes how to make hGH from an hGH precursor.

In a further embodiment the growth hormone is MEAE (SEQ ID 16)-hGH(L101C), which is a precursor of an hGH analogue, wherein the leucine at position 101 in the hGH molecule is substituted by cysteine.

In another embodiment the glucagon-like peptide is GLP-1, GLP-1 and/or derivatives thereof.

The term "glucagon-like peptide" as used herein means the glucagon family of peptides, exendins and analogues thereof. The glucagon family of peptides are encoded by the preproglucagon gene and encompasses three small peptides with a high degree of homology, i.e. glucagon (1-29), GLP-1 (1-37) and GLP-2 (1-33). Exendins are peptides expressed in lizards and like GLP-1, are insulinotropic. Examples of exendins are exendin-3 and exendin-4.

The term "glucagon-like peptide analogue" as used herein refers to a modified glucagon-like peptide wherein one or more amino acid residues of the glucagon-like peptide have been substituted by other amino acid residues and/or wherein one or more amino acid residues have been deleted from the glucagon-like peptide and/or wherein one or more amino acid residues have been added to the glucagon-like peptide. Such addition or deletion of amino acid residues can take place at any position of the peptide.

Experimental Part

For the preparation of glycerol stocks of the strains, a single colony was transferred into a 12 ml test tube containing 2 ml of LB medium with the appropriate antibiotics and grown at 37° C., with shaking at 220 rpm for 2 hours.

For the preparation of fermentation inoculae, the cells from a glycerol stock were streaked on LB plates with and without addition of ampicilin. The overnight cells were washed with LB medium and inoculated into 500 ml shake flasks containing 100 ml each of fermentation complex medium with appropriate antibiotic concentration and grown at 37° C. with shaking at 220 rpm for 3-4 hours. The cells were then inoculated into the reactor to a concentration of approximately 0.5 $OD_{600}$.

Fermentations were conducted under aerobic conditions in a 5l bioreactor with an initial volume of fermentation complex medium of 2.5l, with appropriate antibiotics. At time zero, the reactor was inoculated to an $OD_{600}$ of approximately 0.5. The pH was maintained at 7.0 with 5N $NH_3$ and $H_2SO_4$ and a constant air flow rate of 6 ml/min. was sparged through the culture during the fermentation period. The temperature was maintained at 37° C. The agitation was cascade-controlled by maintaining dissolved oxygen level up to 20% of saturated $O_2$.

A fed-batch experiment was performed to compare the growth and peptide expression of group II deleted strain with its parental strain in a high density fermentor. The fermentor was charged with complex medium supplemented with 27 g/l of glycerol. At time zero, the fermentor was inoculated to an $OD_{600}$ of 0.5. Glycerol and yeast extract were added continuously in increasing steps as basic glycerol was consumed, which was indicated by an increase in dissolved oxygen. The samples for determination of $OD_{600}$ and protein expression were collected from the fermentor and analyzed by spectrophotometer and by SDS-PAGE.

Induction of protein expression in bacteria is well known in the art. In the present invention the induction of protein expression is made by addition of isopropyl-β-Dthiogalacto-pyranoside (IPTG).

Plasmids and strains used in certain embodiments of the invention are listed in Tables 1 and 2, respectively. The construction of plasmids was performed using standard molecular biology techniques as described in Sambrook et al. [A Laboratory Manual (1989) CSH].

TABLE 1

Plasmids used in the examples

| Plasmid | Genotype | Origin |
|---|---|---|
| pKD46 | $Amp^R$ | E coli Genetic Stock Center |
| pCP20 | $Amp^R Cm^R$ | E. coli Genetic Stock Center |
| pEZ-T | Cloning vector $Amp^R$ | GenStar |
| pGEM-T | Cloning vector $Amp^R$ | Promega |
| pNNC1-g (pET11d-MEAE-hGH) | Expression vector $Amp^R$ expressing MEAE-hGH | Based on pET 11d from Novagen |
| pNNC1-1h (pET11d-MEAE-hGH, alr (alr promoter and coding sequence) | Expression vector alr Expressing MEAE-hGH and D,L-alanine racemase | Based on pET 11d from Novagen |

TABLE 2

Strains used in the examples

| Strain | Genotype | Reference |
|---|---|---|
| BL21(DE3) | F-ompT hsd$S_B$(rB-mB-)gal dcm (DE3) | Novagen |
| BL21(DE3)ΔalrΔdadx | F-ompT hsd$S_B$(rB-mB-)gal dcm (DE3)ΔalrΔdadx | WO2008/025744 |
| BL21(DE3)Δ(kpsM-kpsF)::cat | F-ompThsd$S_B$(rB-mB-)galdcm(DE3)Δ(kpsM-kpsF)::cat | Present invention |
| BL21(DE3)ΔdadXΔalrΔkpsM-kpsF)::cat | F-ompThsd$S_B$(rB-mB-galdcm(DE3)ΔaldΔdadxΔ(kpsM-kpsF)::cat | Present invention |
| BL21(DE3)Δ(kpsM-kpsF) | F- ompT hsd$S_B$(rB-mB-)galdcm(DE3)Δ(kpsM-kpsF) | Present invention |
| BL21(DE3) ΔdadXΔalr Δ(kpsM-kpsF) | F-ompThsd$S_B$(rB-mB-)galdcm(DE3)ΔalrΔdadx Δ(kpsM-kpsF) | Present invention |

TABLE 3

List of primers used to carry out the invention

| PRIMER NAME | CONCENSUS 5' TO 3' (DNA DOUBLE STRANDED) |
|---|---|
| LA_BL_GII_F | SacII + LA<br>TCCTTACCGCGGGTCAAACCCGCTTACCGGGC (SEQ ID 1) |
| LA_BL_GII_R | EcoRI + LA down<br>CTACCGGAATTCTTGATGATGTGATCCTAATCTC (SEQ ID 2) |
| RA1_BL_GII_F | BamHI + RA1<br>TTCGGATCCATCAGCTCCTTTGCACGGAA (SEQ ID 3) |
| RA1_BL_GII_R | SacI + RA1 down<br>GAACGAGCTCACACTCCCGAATCATCAATA (SEQ ID 4) |
| RA_SEQ_R1 | GCACCACTAATTCTTAAGAACCCGCCCACAAG (SEQ ID 5) |
| LA_SEQ_F1 | ACTGGAATTTGGACGGGGGTAGGTATTGCC (SEQ ID 6) |
| LA_SEQ_F2 | TTGATGTCAGTGCTGCTGAGAAGCCTGGGATG (SEQ ID 7) |
| Cat_SEQ_F | CGACGATTTCCGGCAGTTTCTAC (SEQ ID 8) |
| CAT_ID_R | GCCAGGTTTTCACCGTAACACGCC (SEQ ID 9) |
| RA6_BL_GII_F | BamHI + RA6<br>CCTGTGGATCCAGAACGTTGTTG (SEQ ID 10) |
| RA6_BL_GII_R | SacI + RA6 down<br>GAACGAGCTCATGTTGATAAAAGTGAAGTC (SEQ ID 11) |

EXAMPLES

Example 1

Construction of Replacement Cassette

The *E. coli* B BL21(DE3) strain was used as a source of DNA for PCR amplification. Oligonucleotide primers (LA_BL_GII_F/LA_BL_GII_R) (Table 3) were synthesized, targeting a 1001bp region upstream of the 5' end of KpsM containing SacII/EcoRI cloning site. This region was amplified from genomic DNA as left arm (LA). For the right arm (RA), oligonucleotide primers (RA1_BL_GII_F/RA1_BL_GII_R) (Table 3) were synthesized, targeting a 1108 bp region upstream of the 5' end of KpsF containing BamHI/SacI cloning site. PCR products of the left arm and the right arm were generated. The DNA amplification reaction was performed in a thermal cycler, using a program that included the following parameters: denaturation at 94° C. for 50 s, annealing at 57° C. for 60 s and primer extension at 72° C. for 60 s, for a total of 30 cycles. The PCR amplification product with correct band size was observed by gel electrophoresis on a 1% agarose gel, from which 50 µl of the amplified product were extracted from the gel and used to construct a replacement fragment. A list of oligonucleotide sequences is shown in Table 3.

The amplified left arm was gel-purified and ligated into plasmid pEZ-T, resulting in plasmid pEZ-T-LA. The restriction enzymes EcoRI/BamHI digested the FRT-cat-FRT fragment which was ligated into EcoRI/BamHI site of pEZ-T-LA, resulting plasmid pEZ-T-LAFRT-cat-FRT. The amplified right arm was ligated into plasmid pGEM-T and was digested with BamHI/SacI. The BamHI/SacI-digested DNA fragment, which carries an ampicillin resistance gene was ligated into plasmid pEZ-T-LA-FRT-cat-FRT. The chloramphenicol resistance gene provides a selectable marker for identifying the replacement fragment. The resulting plasmid pEZ-T-LA-FRT-cat-FRT-RA, was used to produce a knockout BL21 (DE3) strain.

Example 2

Production of a Knock Out BL21(DE3) Strain

*E. coli* BL21(DE3) was grown in LB medium overnight at 37° C. and the heat shock competent cells of BL21(DE3) were prepared by standard methods. The plasmid pKD46 was transformed into BL21(DE3) competent cells and the transformed cells were grown to 0.4 $OD_{600nm}$ in LB broth supplemented with 100 µg/ml ampicillin at 30° C. The expression of Red recombinase was induced by L-arabinose (final concentration 1 mmol/l) for one hour.

For group II gene cluster knock out, 500 ng of replacement fragment amplified from pEZ-T-LA-FRT-cat-FRT-RA were transferred into BL21(DE3) competent cells by electroporation. The electrotraporation competent cells were prepared by standard methods. Recovery of the cells was carried out at 30° C. for 1.5 hours. The cells were plated on LB agar supplemented with 8 µg/ml chloramphenicol. Chloramphenicol-resistant colonies of BL21(DE3)ΔkpsM-kpsF)::cat were formed after overnight incubation at 30° C.

To ensure complete knock out of the group II gene cluster at the right position of the chromosome, oligonucleotide primers were designed with homology to the outside of the left and the right arms of the group II gene cluster. Lacking the flanking sequences of *E. coli* B BL21(DE3) outside the 18 kb, the published sequence of *E. coli* 536 (Accession no. CP 000247.1) was used for design of the PCR screening primers, assuming a similar location of group II cluster in the 2 genomes, based on high homology in the near flanking regions. Three chloramphenicol-resistant colonies were tested for gene replacement.

Phenotype test of chloramphenicol-resistant colonies was performed by growth in LB+Cm (25 µg/ml) for at least two generations. All of the chloramphenicol-resistant colonies could grow very well in LB+Cm (25 µg/ml) medium. Chloramphenicol-resistant D-alanine auxotrophic strains have also been tested in the same process with supplementation of D-alanine.

A successful replacement was confirmed by bands of 1686 bp and 1578 bp.

Figure 3:
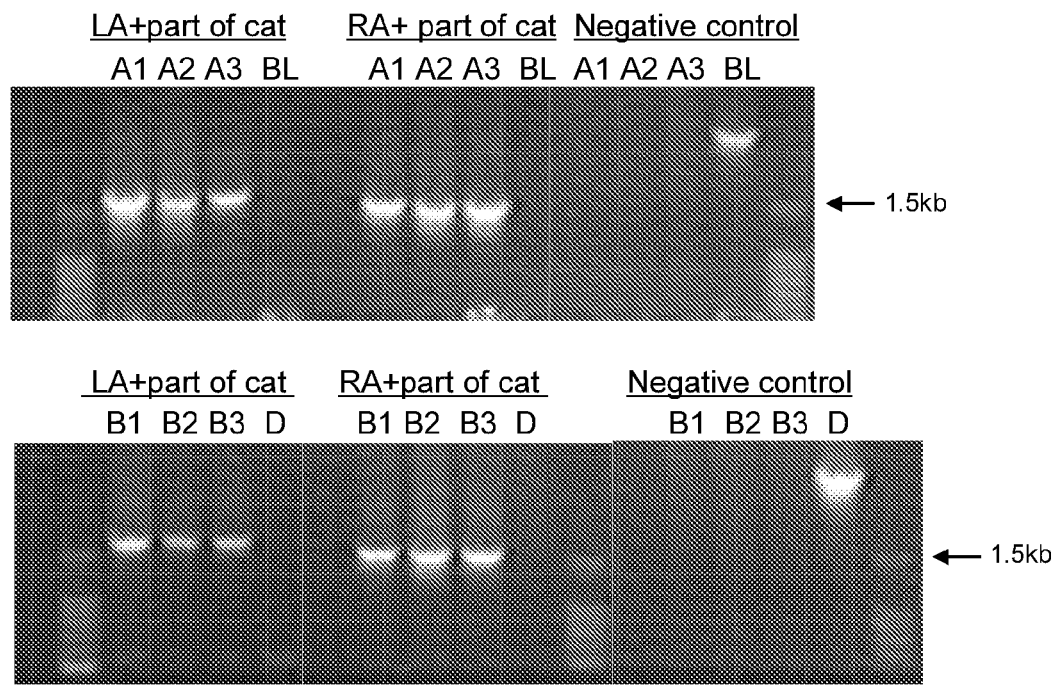
FIG. 3. shows PCR screening of knock out candidates. The right size of 1686 bp (LA+part of cat, A1-A3 in upper panel, B1-B3 in lower panel) and 1578 bp (RA+part of cat, A1-A3 in upper panel, B1-B3 in lower panel) amplified from knockout candidates (but not its parental strain) (BL or D) indicate a successful knock out of group II gene cluster. For the negative control, only the parental strain has a band with size around 3 kb but not group II knock out strain. BL standard for BL21 (DE3), D standard for BL21(DE3)Δ dadXΔalr strain. A1-A3 are different colony numbers of BL21(DE3) knock out candidates and B1-B3 are knock out candidates of BL21(DE3) ΔdadXΔalr strain.

Oligonucleotide primers (LA_SEQ_F1/Cat_ID_R) were used to amplify a band containing left arm and part of cat gene (size 1686 bp), and oligonucleotide primers (RA_SEQ_R1/Cat_SEQ_F) were used to amplify a band containing right arm and part of the cat gene (size 1578 bp). For three chloramphenicol-resistant colonies right size of the bands indicated that the 16 kb group II gene cluster had been replaced by the cat gene (FIG. 3). A negative control of 3000 by band which contained the right arm including kpsF and part of kpsE, was created and should appear only in the control strain (before replacement) but not in the chloramphenicol-resistant strain. Oligonucleotide primers (RA6_BL_GII_F/RA6_BL_GII_R) (Table 3) were used to amplify kpsF and kpsE. The PCR results showed that only the control strain had this band, not the chloramphenicol-resistant strain.

The same elimination process was applied to the D-alanine auxotrophic strain BL21(DE3)ΔdadxΔalr, which needs a supplement of D-alanine during growth in LB medium.

The chloramphenicol-resistant strains $E.$ $coli$ B BL21 (DE3) Δ((kpsM-kpsF)::cat and BL21(DE3)Δ dadX Δ alr Δ(kpsM-kpsF)::cat were confirmed by their phenotype and PCR screening, confirming that the group II capsular gene cluster had been replaced by the cat gene.

Example 3

Elimination of Drug-Resistant Marker and Characterization of group II Knock Out Strain $E.$ $coli$ BL21(DE3)Δ(kpsM-kpsF)::cat and BL21(DE3) ΔdadXΔalr (kpsM-kpsF)::cat cells from frozen stock were grown in LB medium overnight at 37° C. with 25 µg/ml chloramphenicol or 25 µg/ml chloramphenicol, plus 100 mM D-alanine for the second strain. The electroporation competent cells of the two knock out strains were prepared by standard methods. The plasmid pCP20 ($Cm^R$, $Amp^R$) was transformed into the two knock out competent strains. The elimination of the drug-resistant marker was carried out by growing the transformed cells in SOC broth at 30° C. for 1 hour with gentle shaking. The single colonies of ampicillin resistant candidate clones on the plate were selected after overnight culture at 30° C. The candidate clones were grown in LB medium only or LB medium supplemented with D-alanine at 37° C. for three hours, to eliminate the plasmid pCP20. Five single colonies, which appeared on LB medium only or LB medium supplemented with D-alanine, were further characterized by PCR screening.

Phenotype testing of cat elimination strains was performed by growing the single colonies in LB, LB+Cm (8 µg/ml) and LB+Amp. All the cat elimination colonies could grow only on LB medium. For cat eliminated D-alanine auxotrophic strains, all five colonies could grow only in LB medium with supplementary D-alanine. Thus, the cat gene had been eliminated.

A successful elimination of the cat gene should be confirmed by a 2381 bp band. Oligonucleotide primers (LA_SEQ_F2/RA_SEQ_R1) were used to amplify a band containing left arm and right arm. For all the single colonies, the appearance of a 2381 bp band indicated that the cat gene had been eliminated.

The knock out strains $E.$ $coli$ B BL21(DE3)Δ(kpsM-kpsF) and B BL21(DE3)Δ dad X Δalr Δ (kpsM-kpsF) were confirmed by their phenotype and PCR screening. Glycerol stocks of both strains were prepared for storage.

Example 4

Growth of the Knock Out Host Strains in Shake Flask $E.$ $coli$ B BL21(DE3) and B BL21(DE3)Δ(kpsM-kpsF) cells from frozen stocks were grown on LB plate overnight at 37° C. Appropriate amounts of cells washed out from overnight plates were inoculated into 250 ml baffled shake flasks containing 25 ml LB medium to a concentration of approximately 0.05 $OD_{600}$. The cells were grown at 37° C. with shaking at 220 rpm for 8 hours. A sample of each strain was taken every ½ hour to compare the growth of the cells at $OD_{600}$.

The same working flow was applied to $E.$ $coli$ B BL21 (DE3)ΔdadXΔalr and B BL21(DE3)ΔdadXΔalrΔ(kpsM-kpsF) supplemented with D-alanine for comparison of growth in shake flask.

Figure 4:
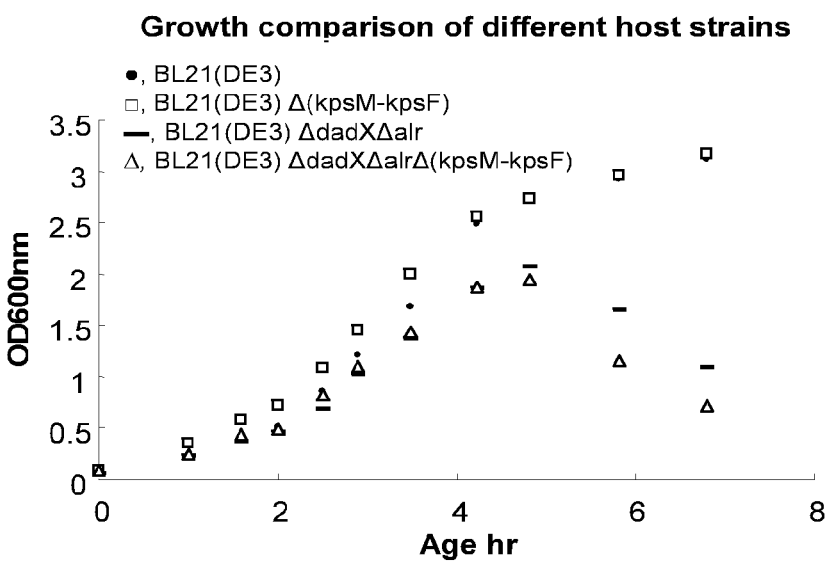
FIG. 4. is a comparison of the growth of host *E. coli* B strains in shake flask. The symbols used refer to the following strains: ●, BL21(DE3); □, BL21(DE3)Δ (kpsM-kpsF); ■, BL21(DE3) ΔdadX Δalr; Δ, BL21(DE3) ΔdadX Δa*l* rΔ(kpsM-kpsF).

The results in FIG. 4 show that growth of BL21Δ(kpsM-kpsF) over time was identical to its parental strain BL21 (DE3) in shake flask using LB medium. The same conclusion could be drawn when comparing BL21(DE3) ΔdadX Δalr Δ (kpsM-kpsF) with BL21(DE3) ΔdadX Δalr.

Example 5

Comparison of Growth and MEAE-hGH Expression Between Host Strain BL21(DE3) and BL21(DE3) Δ kpsM-kpsF) in High Density Fermentation $E.$ $coli$ B BL21(DE3)Δ (kpsM-kpsF) cells from frozen stock were grown on LB plates. Heat shock competent cells of the knock out strain were prepared by standard methods. The plasmid pNNC1-g (pET11d-MEAE-hGH($Amp^R$)) containing an expression cassette of hGH was transformed into B BL21(DE3)Δ(kpsM-kpsF) competent cells, from which a glycerol stock of transformed cells was prepared.

High density fermentations were conducted under aerobic conditions as described above.

Figure 5:
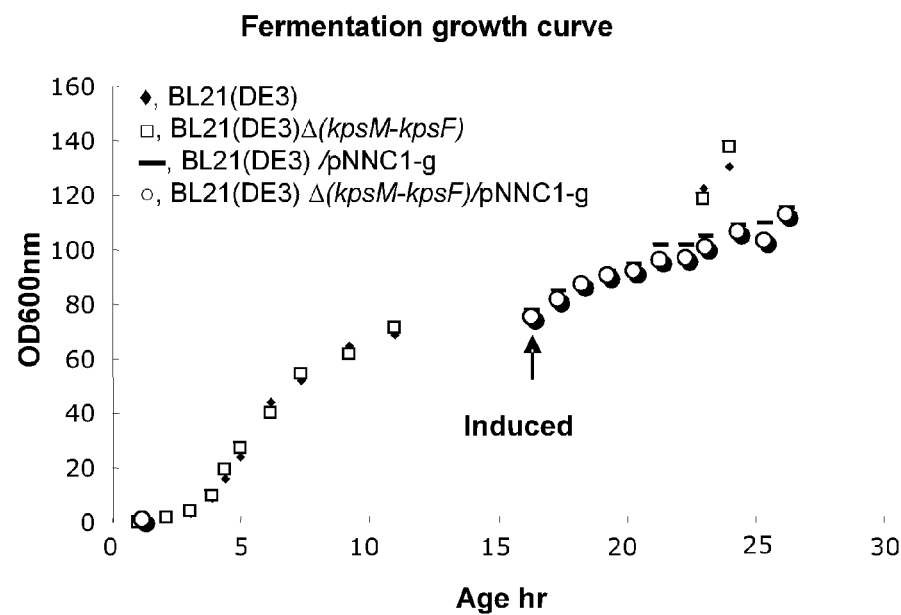
FIG. 5. shows the fermentation growth curve for the different *E. coli* B strains. The symbols used refer to the following strains: ♦, BL21(DE3); □, BL21(DE3)Δ(kpsM-kpsF); ■ BL21(DE3)/pNNC1-g; ○, BL21(DE3)Δ(kpsM-kpsF)/ pNNC1-g.

FIG. 5 shows that the growth of BL21Δ(kpsM-kpsF) over time was identical to its parental strain BL21(DE3) in high density fermentor in complex medium. The same conclusion could be drawn when comparing BL21(DE3)Δ (kpsM-kpsF)/pNNC1-g with BL21(DE3)/pNNC1-g. The cell density reached approximately 140 $OD_{600}$ in the uninduced state. Expression of hGH was carried out by adding IPTG to a concentration of 1 mM when the growth of cells reached 80 $OD_{600}$. After 10 hours of IPTG induction at 30° C., the cell density reached approximately 100 $OD_{600}$.

Figure 6:
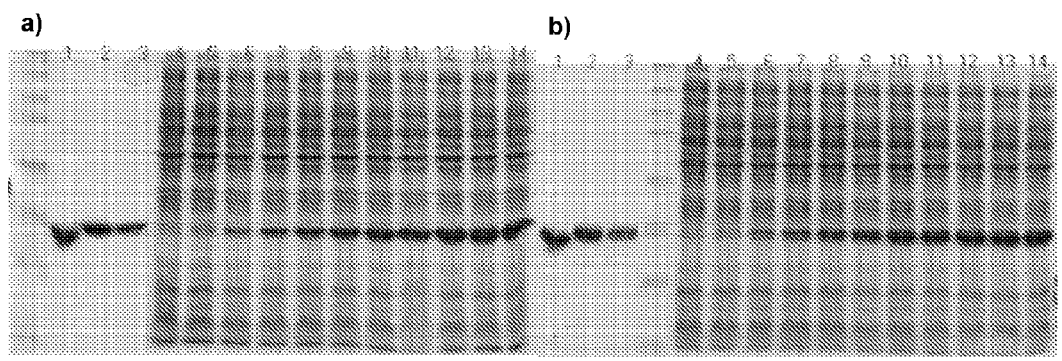
FIG. 6. shows a SDS-polyacrylamide gel electrophoresis (PAGE) of hGH expression at different induction times: a) expression in *E. coli* B BL21(DE3)/pNNC-1g and b) expression in *E. coli* B BL21(DE3)Δ(kpsM-kpsF)/pNNC1-g. In both a) and b), lanes 1-3 show different concentrations of hGH: 5 μg, 2.5 μg and 1.25 μg, respectively. Lane 4 shows expression of hGH before induction and lanes 5-14 show the expression of hGH at different induction times from 1-10 hours, every hour. All the samples were normalized to the same loading OD.

$E.$ $coli$ B BL21(DE3)/pNNC1-g and B BL21(DE3)Δ (kpsM-kpsF)/pNNC1-g are efficient in the production of hGH as seen on SDS-PAGE. The increase in hGH expression level follows increasing induction time from 1 to 10 hours shown on the SDS-PAGE gel (FIG. 6). The ability of the two strains to produce hGH was identical, i.e., no significant difference was observed in the expression of hGH by host strain B BL21(DE3)Δ(1 cpsM-kpsF) when compared to B BL21(DE3), harbouring the gene II cluster.

Example 6

Comparison of Growth and MEAE-hGH Expression Between Host Strain BL21(DE3)ΔalrΔdadX and BL21(DE3)Δalr ΔdadXΔ(kpsM-kpsF) in high density fermentation E. coli B BL21(DE3) ΔdadXΔalrΔ (kpsM-kpsF) cells from frozen stock were grown in LB medium supplemented with D-alanine. Heat shock competent cells of the knock out strain were prepared by standard methods. The pNNC1-1h (pET11d-MEAE-hGH and alrP-alrCD (Amp$^R$)) containing a D-alanine complementary gene was digested using AatII/PsiI, following by blunt end and self-ligation of the plasmid, resulting in a bla-plasmid for selection of the alr gene on the plasmid. The plasmid pNNC1-1h (pET11d-MEAE-hGH, alrP-alrCD, bla-) was transformed into BL21(DE3)ΔdadXΔalrΔ(kpsM-kpsF) competent cells. Colonies appearing overnight on LB plate without supplementary D-alanine were isolated for the preparation of glycerol stocks.

High density fermentations were conducted as described in Example 5.

Figure 7:
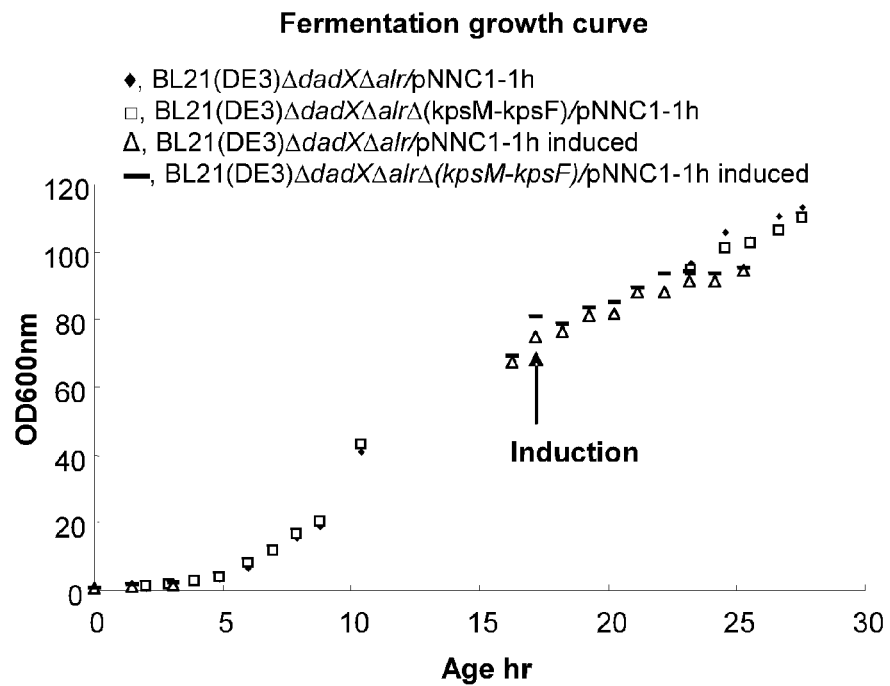
FIG. 7. shows the growth of the different *E. coli* B strains before and after induction of hGH expression. The symbols used refer to the following strains: ♦: BL21(DE3) ΔdadXΔa*l* r/pNNC1-1h; □: BL21ΔdadXΔa*l* rΔ(kpsM-kpsF)/pNNC1-1h; Δ, BL21 (DE3)ΔdadX Δalr/pNNC1-1h induced; ■, BL21(DE3)ΔdadXΔalrΔ(kpsM-kpsF)/pN NC1-1h induced.

FIG. 7 shows that the growth of E. coli B BL21(DE3) ΔdadXΔa l rΔ(kpsM-kpsF)/pNNC1-1h over time was identical to its parental strain BL21(DE3)ΔdadXΔa l r/pNNC1-1h in a high density fermentor in FCM1 medium. The same conclusion could be drawn under induction of hGH when comparing B BL21(DE3)ΔdadXΔa l r/pNNC1-1h with BL21(DE3)ΔdadXΔalrΔ(kpsM-kpsF)/pNNC1-1 h. The cell density reached approximately 120 $OD_{600}$ in the uninduced state. Expression of hGH was carried out by adding IPTG to a concentration of 1 mM when the growth of cells reached 80 $OD_{600}$. After 9 hours of IPTG induction at 30° C., the cell density reached approximately 100 $OD_{600}$.

Figure 8:
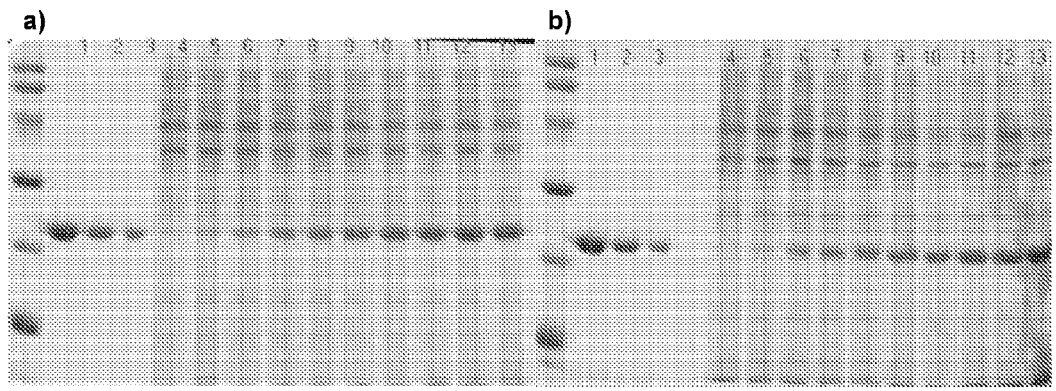
FIG. 8. shows the expression of hGH analyzed by SDS-PAGE at different induction times: a) *E. coli* B BL21 (DE3)ΔdadXΔa*l* r/pNNC1-1h; b) *E. coli* B BL21(DE3) ΔdadX Δa*l* rΔ(kpsM-kpsF)/pNNC1-1h. In both a) and b), lanes 1-3 show expression of hGH at different concentrations, 5 μg, 2.5 μg and 1.25 μg, respectively. Lane 4 shows expression of hGH before induction and lanes 5-13 show the expression of hGH at induction times from 1-9 hours, every hour. All samples were normalized to the same loading OD.

E. coli B BL21(DE3)ΔdadXΔalr/pNNC1-1h and B BL21(DE3)ΔdadXΔalrΔ (kpsM-kpsF)/pNNC1-1h were efficient in production of hGH as can be seen from the results by SDS-PAGE (FIG. 8). Increase in hGH expression level follows increasing induction time. Both strains had identical ability to produce hGH.

Example 7

Evaluation of Cell Growth and Expression of MEAE-hGH(L101C) using host strain E. coli B BL21(DE3)ΔalrΔdadXΔ(kpsM-kpsF) in High-Cell Density Fermentation E. coli B BL21(DE3) ΔdadXΔalrΔ (kpsM-kpsF) cells from frozen stock were grown in LB medium supplemented with D-alanine. Competent cells of this triple knock-out strain for transformation using heat-shock method were prepared by standard methods.

To delete the β-lactamase gene coding for ampicilin-resistance, the plasmid pNNC1a.23 (pET11d-MEAE-hGH (L101C) encoding MEAE-hGH(L101C) and containing alrP-alrCD for complementing the D-alanine-deficiency of the host cell was digested using AatII/PsiI, followed by end-blunting and self-ligation for removal of the β-lactamase gene. The resulting plasmid, pNNC1a.23 (pET11d-MEAE-hGH, alr, bla-), was transformed into the host cell, BL21 (DE3)ΔdadX6alrΔ(kpsM-kpsF), by heat-shock method. A single colony grown up from LB plate without supplementation with D-alanine was selected to prepare the glycerol stocks for storage at −80° C.

Figure 9:
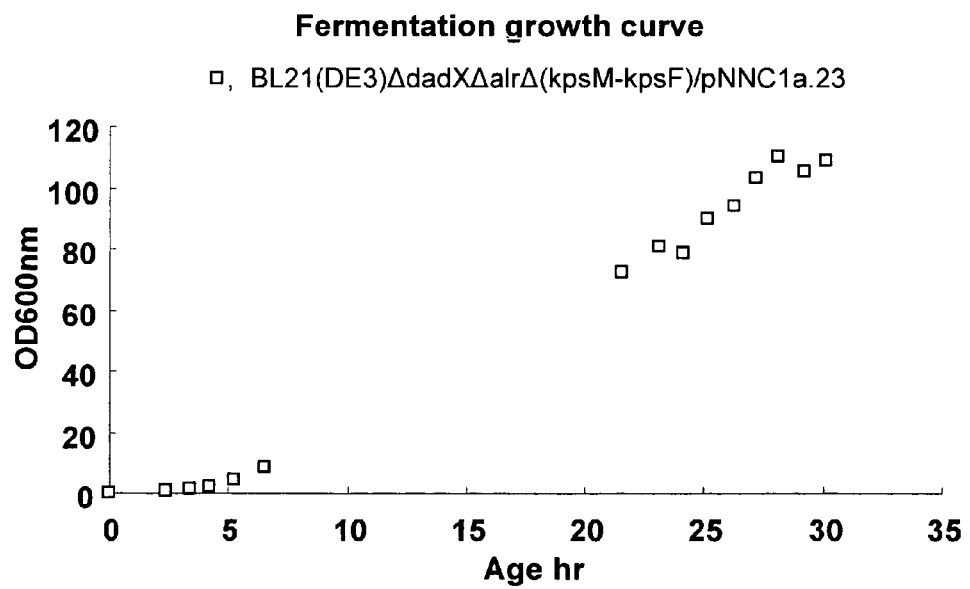
FIG. 9. shows the growth curve of *E. coli* B BL21(DE3) ΔdadXΔa*l* rΔ(kpsM-kpsF)/pNNC1a.23 in a high cell-density fermentation in FDM1-2 medium. Expression of hGH mutant, MEAE-hGH(L101C), was induced by adding IPTG to a final concentration of 0.2 mM when the cell density reached 70 $OD_{600}$ and continued to cultivate at 25° C. The final cell density reached approximately 100 $OD_{600}$ after 8 hours' induction.

Two batches of high-cell density fermentation were conducted as described in Example 5. Cell growth was monitored during the process and the results are shown in FIG. 9.

Figure 10:
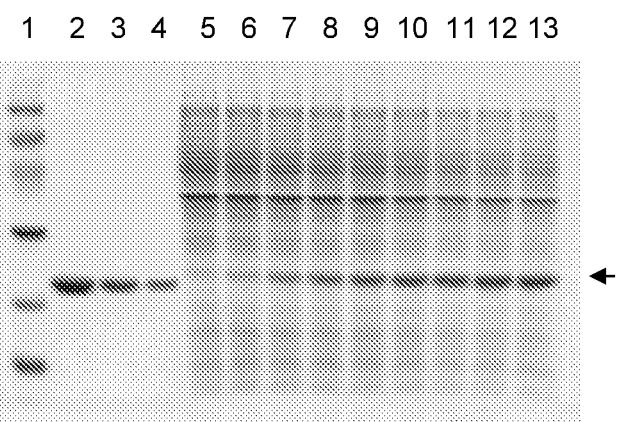
FIG. 10. shows expression of MEAE-hGH(L101C) during high-cell density fermentation. Lane 1: marker; lanes 2-4: purified hGH as the standard at concentrations of 5, 2.5, 1.25 μg, respectively; lanes 5-13: samples taken at different time intervals after being induced for 0, 1, 2, 3, 4, 5, 6, 7 and 8 hours, respectively. Arrow indicates the target protein, MEAE-hGH(L101C).

Expression of MEAE-hGH(L101C) by strain E. coli B BL21(DE3)ΔdadXΔalrΔ (kpsM-kpsF) harbouring plasmid pNNC1a.23 was evaluated in high-cell density fermentation. The result showed that the cell density at harvest can reach to about 100 measured at $OD_{600nm}$, and the expression level of the target protein, MEAE-hGH(L101C), reached about 7 g/l after 8 hours' induction, as shown in FIG. 10.

Example 8

Expression of *Arthrobacter ureafaciens* sialidase in E. coli BL21(DE3)Δ(kpsM-kpsF)

*Arthrobacter ureafaciens* sialidase (AUS, 53.4 kDa theoretical mass) was produced in *Escherichia coli* BL21(DE3)Δ (kpsM-kpsF) with a C-terminal His-tag. The *Arthrobacter ureafaciens* sialidase gene, with a His6-tag in the C-terminus, was cloned in expression vector pET-24a (Novagen) under control of the T7 promoter. In order to produce the sialidase enzyme from *Arthrobacter ureafaciens* a synthetic codon optimized gene encoding the following protein sequence was generated (SEQ ID 12):

MAPTPPNSPTLPPGSFSETNLAADRTAANFFYRIPALTYLGNDVVLAAW

DGRPGSAADAPNPNSIVQRRSTDGGKTWGPVQVIAAGHVADASGPRYGY

SDPSYIYDAEANKVFAFFVYSKDQGFGGSQFGNDDADRNVISSAVIESS

DAGVTWSQPRLITSVTKPGTSKTNPAAGDVRSNFASSGEGIQLKYGPHK

GRLIQQYAGDVRQADGSNKIQAYSVYSDDHGVTWHKGANVGDRMDENKT

VELSDGRVLLNSRDNANRGYRKVAVSTDGGATYGPVSQDTELPDPANNG

AIARMFPNAAQGSADAKKLIFTNANSKTGRENVSARVSCDDGETWPGVR

TIRSGFSAYSTVTRLADGKFGVLYEGNYTDNMPFATFDDAWLNYVCAPL

AVPAVNIAPSATQEVPVTVTNQEATTLSGATATVYTPSGWSATTVPVPD

VAPGASVTVTVALTAPADASGPRSLNAAFTTADGRVSQFTFTATTPVAP

QVGLTITGSALEHHHHHH

The synthetic gene was introduced into the pET-24a expression vector as a XbaI-XhoI fragment to produce the AUS expression vector pLLC028. The resulting vector was transformed into competent BL21(DE3),6(kpsM-kpsF) and transformants were preserved in glycerol at −80° C.

One cryotube of the frozen initial cell clone (ICC) was used to inoculate two yeast extract media (yeast extract 5 g/l, glucose 10 g/l, agar 20 g/l) agar flask. The agar medium contained kanamycin for selection. Incubation was at 30° C. for 25 hours. After incubation, the cells were washed from the agar surface using sterile 0.9% NaCl solution. A 10 l fermentation was inoculated using pre-culture from two agar flasks. The volume of the obtained inoculum was 75 m, and the $OD_{600nm}$ was 4.3, resulting in a start $OD_{600nm}$ in the fermentor of approximately 0.03. The fermentation was carried out in a 20 l stainless steel vessel with a start working volume of 10 l. The fermentation starts with a 8 hour long batch phase on a complex medium containing 40 g/l yeast extract, 15 g/l glycerol (87%), salts and trace metals, followed by glycerol feeding at a predetermined profile. During the first 17 hours, fermentation temperature was 37° C. After that, the temperature was lowered to 30° C. At 18 hours elapsed fermentation time, the inducer IPTG was added at 0.1 mM in order to induce protein expression. The duration of induction can be up to 22 hours. The recovery process consists of centrifugation, high pressure homogenisation and crossflow microfiltration using Sartocon Slice Cassettes with a pore size of 0.2 µm.

Figure 11:
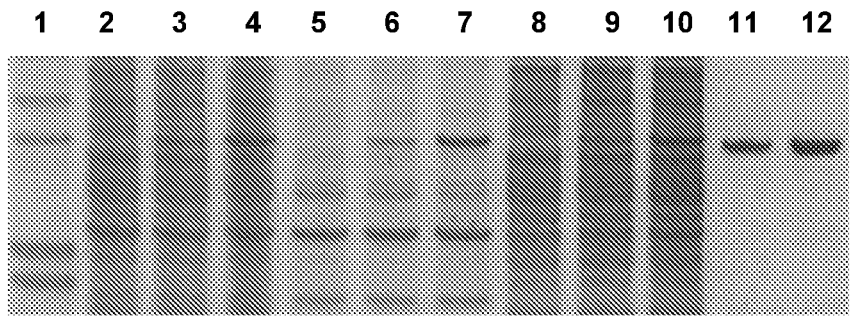
FIG. 11. shows SDS-PAGE analysis of fermentation samples from expression of *Arthrobacter ureafaciens* sialidase in *E. coli* B BL21(DE3)Δ(kpsM-kpsF). Lane 1: marker; lane 2: pre-induction, homogenate; lane 3: post-induction, homogenate; lane 4: final sample, homogenate; lane 5: pre-induction, insoluble fraction; lane 6: post-induction, insoluble fraction; lane 7: final sample, insoluble fraction; lane 8: pre-induction, soluble fraction; lane 9: post-induction, soluble fraction; lane 10: final sample, soluble fraction; lanes 11-12: sialidase standard (150 and 300 mg/l). All samples were 10× diluted.

The AUS fermentation was analysed using SDS-PAGE and an enzymatic activity assay. SDS-PAGE analysis revealed that the expressed sialidase appears both in the soluble and pellet fraction after bead-milling. FIG. 11 shows a typical fermentation result from a 10 L batch run at 30° C. induction temperature and 0.1 mM IPTG.

Example 9

Expression of Human Fibroblast Growth Factor 21 (FGF21) in BL21 DE3 and BL21 DE3Δ(kpsM-kpsF)

The DNA and amino acid sequences for human FGF21 are disclosed by e.g., Nishimura et al in Biochim. Biophys. Acta 1492(1):203-206 (2000). The sequences are also available from public databases (Accession nos. EMBL:AB021975 and UNIPROT:Q9NSA1, respectively).

The native polypeptide is synthesised with a signal peptide (in italics below) of 28 amino acids for secretion, while the mature FGF21 polypeptide consists of the remaining 181 amino acids (SEQ ID 13):

*MDSDETGFEHSGLWVSVLAGLLLGACQAHPIPDSSPLLQFGGQVRQRYL*

YTDDAQQTEAHLEIREDGTVGGAADQSPESLLQLKALKPGVIQILGVKT

SRFLCQRPDGALYGSLHFDPEACSFRELLLEDGYNVYQSEAHGLPLHLP

GNKSPHRDPAPRGPARFLPLPGLPPA-LPEPPGILAPQPPDVGSSDPLS

MVGPS QGRSPSYAS

The mature FGF21 polypeptide was cloned and expressed as an intracellular protein in *E. coli*, without the signal peptide, but with an added N-terminal methionine. In particular, a 550 by coding region including at the 3'-end the ATG codon for Met, as well as Nde1 and BamH1 restriction sites at the 3'- and 5'-ends, respectively, were inserted into the expression vector pET 11c (Novagen) in Nde1-BamH1 under control of the phage T7 promoter, and transformed into *E. coli* B BL21 (DE3) and into *E. coli* B BL21 DE34(kpsM-kpsF). The cells were grown in LB amp 100 µg/ml to $OD_{450}$ 0.5, and expression was induced with 0.3 mM IPTG for 4 hours at 37° C. Crude extracts of cells were made by sonication for analysis of FGF21 expression.

Figure 12:
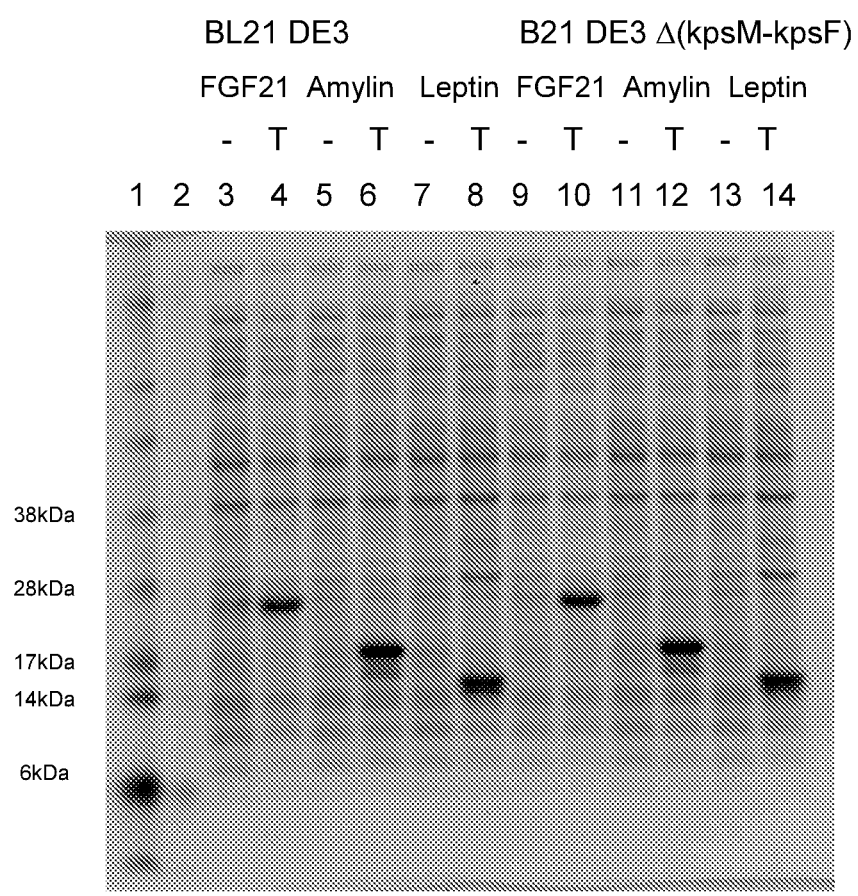
FIG. 12. shows expression of FGF21, amylin and leptin all from *H. sapiens* in *E. coli* B BL21 DE3 and in *E. coli* B BL21 DE3Δ(kpsM-kpsF). Lane 1: marker; lanes 3-8: expression in BL21 DE3; lanes 9-14: expression in BL21 DE3 Δ(kpsM-kpsF); lanes 3 and 9: uninduced; Lanes 4 and 10: induced FGF21; lanes 5 and 11: uninduced; lanes 6 and 12: induced amylin; lanes 7 and 13: uninduced; lanes 8 and 14: induced leptin.

The Coomassie stained SDS-PAGE gel in FIG. 12 shows equally successful expression of FGF21 in *E. coli* B BL21 DE3 and *E. coli* B BL21 DE34(kpsM-kpsF). Although the calculated molecular weight (MW) of the thus expressed FGF21 (Met-FGF21) is 19.5 kD, it migrated on the gel as a 25 kD protein, which is likely due to the high content of prolines, delaying the movement of the protein.

The current example shows that the yield for FGF21 is not affected by the genetic manipulation of the host strain.

Example 10

Expression of Human Amylin in BL21 DE3 and BL21 DE34(kpsM-kpsF)

The sequence of the 37 aminoacid amyloid peptide amylin was published by Cooper et al. in Proc. Natl. Acad. Sci. (84): 8628-8632, (1987). The gene was cloned and fused it N-terminally to a ribosomal protein RL23 from *Thermotoga maritima*. The 146 amino acids fusion protein has the following sequence (SEQ ID 14):

KQEKLSLHDVLIRPIITEKALILREQRKYVFEVNPLANKNLVKEAVEKL

FNVKVEKVNILNMKPKPKRRGIFEGKTRSWKKAVVTLKEGYTIKELEGE

HSSSSDDDDKKCNTAT-CATQRLA-NFLVHSSNNFGAILSSTNVGSNTY

The fusion gene was cloned as described in example 9 as a 450 by Nde1-BamH1 fragment into pET 11c under control of the T7 promoter, and the plasmid was transformed into BL21 DE3 and BL21 DE3Δ(kpsM-kpsF).

Expression was performed as described in example 9, and the result is shown in FIG. 12, again demonstrating equally high yield expression in the two *E. coli* B hosts BL21 DE3 and BL21 DE3Δ(kpsM-kpsF).

Example 11

Expression of Human Leptin in BL21 DE3 and BL21 DE3z1(kpsM-kpsF)

The sequence of the 146 amino acids long human leptin was published by Masuzaki et al. in Diabetes (44): 855-858 (1995). The protein is secreted in humans with the addition of a 21 amino acids signal peptide. The mature leptin was expressed intracellularly in *E. coli* has the following sequence (SEQ ID 15):

MVPIQKVQDDTKTLIKTIVTRINDISHTQSVSSKQKVTGLDFIPGLHPI

LTLSKMDQTLAVYQQILTSMPSRNVIQISNDLENLRDLLHVLAFSKSCH

LPWASGLETLDSLGGVLEASGYSTEVVALSRLQGSLQDMLWQLDLSPGC

The leptin gene was cloned as described in example 9 as a 450 by Nde1-BamH1 fragment into pET11c under control of the T7 promoter, and the plasmid was transformed into BL21 DE3 and BL21 DE3Δ(kpsM-kpsF).

Expression was performed as described in example 9, and the result is shown in FIG. 12, again illustrating equally high yield expression in the two *E. coli* hosts BL21 DE3 and BL21 DE3Δ(kpsM-kpsF).

It is concluded that the elimination of group II capsular gene cluster does not affect the growth of the cells in any growth conditions. It can also be concluded that group II capsular gene cluster elimination does not affect protein expression. Therefore, a more safe strain with complete removal of group II capsular gene cluster is hereby produced for using *E. coli* B BL21(DE3) as commercial host strain for therapeutic protein production. The operation of deleting group II capsular genes in *E. coli* B BL21(DE3) brings it into the same safety category as *E. coli* K12, since the group II gene cluster is the only significant difference between the two strains.

The invention claimed is:

1. An *E. coli* B BL21 strain having a permanent deletion of part or all of its group II capsular gene cluster.

2. The *E. coli* B BL21 strain according to claim 1, characterised by having a total deletion of group II capsular gene cluster.

3. The *E. coli* B BL21 strain according to claim 1, wherein the *E. coli* is *E. coli* B BL21(DE3).

4. The E. coli strain according to claim 1, wherein the *E. coli* is *E. coli* B BL21(DE3)ΔdadXΔalr.

5. The *E. coli* B BL21 strain according to claim 1, wherein the strain further comprises an expression vector with an inserted DNA sequence encoding a peptide.

6. The *E. coli* B BL21 strain according to claim 5, wherein the peptide is selected from the group consisting of hGH, glucagon-like peptides, interleukins, insulin analogs, wild-type adiponectin, FGF-21, trypsin, aprotinin, amylin and analogs thereof, leptin and analogs thereof, sialidase, transglutaminase (tGase), HRV (Human Rhino Virus) 3C protease, and Tobacco Etch Virus (TEV) protease.

7. A method for producing an *E. coli* B strain according to claim 1, wherein the group II capsular gene cluster is deleted by a method comprising the steps of:

replacing of group II capsular gene cluster by a selection marker; and eliminating the selection marker.

8. The method for production of an *E. coli* B strain according to claim 7, where the selection marker is an antibiotic resistance gene.

9. The method for production of an *E. coli* B strain according to claim 8, where the antibiotic resistance gene is selected from the group consisting of chloramphenicol, tetracyclin, ampicillin, kanamycin, vancomycin and erythromycin.

10. The method for production of an *E. coli* B strain according to claim 8, where the antibiotic is chloramphenicol.

11. A method for the production of a peptide comprising culturing the *E. coli* B strain according to claim 5 in a suitable culture medium followed by isolation and purification of the expressed peptide.

12. The method according to claim 11 wherein the peptide is hGH.

13. The method according to claim 11 wherein the peptide is FGF-21.

14. The method according to claim 11 wherein the peptide is amylin.

* * * * *

SEQUENCE LISTING

<160> NUMBER OF SEQ ID NOS: 16

<210> SEQ ID NO 1
<211> LENGTH: 32
<212> TYPE: DNA
<213> ORGANISM: Artificial
<220> FEATURE:
<223> OTHER INFORMATION: Oligonucleotides

<400> SEQUENCE: 1
tccttaccgc gggtcaaacc cgcttaccgg gc        32

<210> SEQ ID NO 2
<211> LENGTH: 34
<212> TYPE: DNA
<213> ORGANISM: Artificial
<220> FEATURE:
<223> OTHER INFORMATION: Oligonucleotides

<400> SEQUENCE: 2
ctaccggaat tcttgatgat gtgatcctaa tctc        34

<210> SEQ ID NO 3
<211> LENGTH: 29
<212> TYPE: DNA
<213> ORGANISM: Artificial
<220> FEATURE:
<223> OTHER INFORMATION: Oligonucleotides

<400> SEQUENCE: 3
ttcggatcca tcagctcctt tgcacggaa        29

<210> SEQ ID NO 4
<211> LENGTH: 30
<212> TYPE: DNA
<213> ORGANISM: Artificial
<220> FEATURE:
<223> OTHER INFORMATION: Oligonucleotides

<400> SEQUENCE: 4
gaacgagctc acactcccga atcatcaata        30

<210> SEQ ID NO 5
<211> LENGTH: 32
<212> TYPE: DNA
<213> ORGANISM: Artificial
<220> FEATURE:
<223> OTHER INFORMATION: Oligonucleotides

<400> SEQUENCE: 5
gcaccactaa ttcttaagaa cccgcccaca ag        32

<210> SEQ ID NO 6
<211> LENGTH: 30
<212> TYPE: DNA
<213> ORGANISM: Artificial
<220> FEATURE:
<223> OTHER INFORMATION: Oligonucleotides

<400> SEQUENCE: 6
actggaattt ggacgggggt aggtattgcc        30

<210> SEQ ID NO 7
<211> LENGTH: 28
<212> TYPE: DNA

```
<213> ORGANISM: Artificial
<220> FEATURE:
<223> OTHER INFORMATION: Oligonucleotides

<400> SEQUENCE: 7
aattcttaag aacccgccca caaggcgg                                    28

<210> SEQ ID NO 8
<211> LENGTH: 23
<212> TYPE: DNA
<213> ORGANISM: Artificial
<220> FEATURE:
<223> OTHER INFORMATION: Oligonucleotides

<400> SEQUENCE: 8
cgacgatttc cggcagtttc tac                                         23

<210> SEQ ID NO 9
<211> LENGTH: 24
<212> TYPE: DNA
<213> ORGANISM: Artificial
<220> FEATURE:
<223> OTHER INFORMATION: Oligonucleotides

<400> SEQUENCE: 9
gccaggtttt caccgtaaca cgcc                                        24

<210> SEQ ID NO 10
<211> LENGTH: 23
<212> TYPE: DNA
<213> ORGANISM: Artificial
<220> FEATURE:
<223> OTHER INFORMATION: Oligonucleotides

<400> SEQUENCE: 10
cctgtggatc cagaacgttg ttg                                         23

<210> SEQ ID NO 11
<211> LENGTH: 30
<212> TYPE: DNA
<213> ORGANISM: Artificial
<220> FEATURE:
<223> OTHER INFORMATION: Oligonucleotides

<400> SEQUENCE: 11
gaacgagctc atgttgataa aagtgaagtc                                  30

<210> SEQ ID NO 12
<211> LENGTH: 508
<212> TYPE: PRT
<213> ORGANISM: Arthrobacter ureafaciens

<400> SEQUENCE: 12

Met Ala Pro Thr Pro Pro Asn Ser Pro Thr Leu Pro Pro Gly Ser Phe
1               5                   10                  15

Ser Glu Thr Asn Leu Ala Ala Asp Arg Thr Ala Ala Asn Phe Phe Tyr
                20                  25                  30

Arg Ile Pro Ala Leu Thr Tyr Leu Gly Asn Asp Val Val Leu Ala Ala
            35                  40                  45

Trp Asp Gly Arg Pro Gly Ser Ala Ala Asp Ala Pro Asn Pro Asn Ser
        50                  55                  60

Ile Val Gln Arg Arg Ser Thr Asp Gly Gly Lys Thr Trp Gly Pro Val
65                  70                  75                  80

Gln Val Ile Ala Ala Gly His Val Ala Asp Ala Ser Gly Pro Arg Tyr
```

```
                        85                  90                  95
Gly Tyr Ser Asp Pro Ser Tyr Ile Tyr Asp Ala Glu Ala Asn Lys Val
            100                 105                 110

Phe Ala Phe Phe Val Tyr Ser Lys Asp Gln Gly Phe Gly Gly Ser Gln
            115                 120                 125

Phe Gly Asn Asp Asp Ala Asp Arg Asn Val Ile Ser Ser Ala Val Ile
            130                 135                 140

Glu Ser Ser Asp Ala Gly Val Thr Trp Ser Gln Pro Arg Leu Ile Thr
145                 150                 155                 160

Ser Val Thr Lys Pro Gly Thr Ser Lys Thr Asn Pro Ala Ala Gly Asp
            165                 170                 175

Val Arg Ser Asn Phe Ala Ser Ser Gly Glu Gly Ile Gln Leu Lys Tyr
            180                 185                 190

Gly Pro His Lys Gly Arg Leu Ile Gln Gln Tyr Ala Gly Asp Val Arg
            195                 200                 205

Gln Ala Asp Gly Ser Asn Lys Ile Gln Ala Tyr Ser Val Tyr Ser Asp
            210                 215                 220

Asp His Gly Val Thr Trp His Lys Gly Ala Asn Val Gly Asp Arg Met
225                 230                 235                 240

Asp Glu Asn Lys Thr Val Glu Leu Ser Asp Gly Arg Val Leu Leu Asn
            245                 250                 255

Ser Arg Asp Asn Ala Asn Arg Gly Tyr Arg Lys Val Ala Val Ser Thr
            260                 265                 270

Asp Gly Gly Ala Thr Tyr Gly Pro Val Ser Gln Asp Thr Glu Leu Pro
            275                 280                 285

Asp Pro Ala Asn Asn Gly Ala Ile Ala Arg Met Phe Pro Asn Ala Ala
            290                 295                 300

Gln Gly Ser Ala Asp Ala Lys Lys Leu Ile Phe Thr Asn Ala Asn Ser
305                 310                 315                 320

Lys Thr Gly Arg Glu Asn Val Ser Ala Arg Val Ser Cys Asp Asp Gly
            325                 330                 335

Glu Thr Trp Pro Gly Val Arg Thr Ile Arg Ser Gly Phe Ser Ala Tyr
            340                 345                 350

Ser Thr Val Thr Arg Leu Ala Asp Gly Lys Phe Gly Val Leu Tyr Glu
            355                 360                 365

Gly Asn Tyr Thr Asp Asn Met Pro Phe Ala Thr Phe Asp Asp Ala Trp
            370                 375                 380

Leu Asn Tyr Val Cys Ala Pro Leu Ala Val Pro Ala Val Asn Ile Ala
385                 390                 395                 400

Pro Ser Ala Thr Gln Glu Val Pro Val Thr Val Thr Asn Gln Glu Ala
            405                 410                 415

Thr Thr Leu Ser Gly Ala Thr Ala Thr Val Tyr Thr Pro Ser Gly Trp
            420                 425                 430

Ser Ala Thr Thr Val Pro Val Pro Asp Val Ala Pro Gly Ala Ser Val
            435                 440                 445

Thr Val Thr Val Ala Leu Thr Ala Pro Ala Asp Ala Ser Gly Pro Arg
            450                 455                 460

Ser Leu Asn Ala Ala Phe Thr Thr Ala Asp Gly Arg Val Ser Gln Phe
465                 470                 475                 480

Thr Phe Thr Ala Thr Thr Pro Val Ala Pro Gln Val Gly Leu Thr Ile
            485                 490                 495

Thr Gly Ser Ala Leu Glu His His His His His His
            500                 505
```

-continued

```
<210> SEQ ID NO 13
<211> LENGTH: 209
<212> TYPE: PRT
<213> ORGANISM: Homo sapiens

<400> SEQUENCE: 13
```

Met Asp Ser Asp Glu Thr Gly Phe Glu His Ser Gly Leu Trp Val Ser
1               5                   10                  15

Val Leu Ala Gly Leu Leu Leu Gly Ala Cys Gln Ala His Pro Ile Pro
            20                  25                  30

Asp Ser Ser Pro Leu Leu Gln Phe Gly Gly Gln Val Arg Gln Arg Tyr
        35                  40                  45

Leu Tyr Thr Asp Asp Ala Gln Gln Thr Glu Ala His Leu Glu Ile Arg
    50                  55                  60

Glu Asp Gly Thr Val Gly Gly Ala Ala Asp Gln Ser Pro Glu Ser Leu
65                  70                  75                  80

Leu Gln Leu Lys Ala Leu Lys Pro Gly Val Ile Gln Ile Leu Gly Val
                85                  90                  95

Lys Thr Ser Arg Phe Leu Cys Gln Arg Pro Asp Gly Ala Leu Tyr Gly
            100                 105                 110

Ser Leu His Phe Asp Pro Glu Ala Cys Ser Phe Arg Glu Leu Leu Leu
        115                 120                 125

Glu Asp Gly Tyr Asn Val Tyr Gln Ser Glu Ala His Gly Leu Pro Leu
    130                 135                 140

His Leu Pro Gly Asn Lys Ser Pro His Arg Asp Pro Ala Pro Arg Gly
145                 150                 155                 160

Pro Ala Arg Phe Leu Pro Leu Pro Gly Leu Pro Pro Ala Leu Pro Glu
                165                 170                 175

Pro Pro Gly Ile Leu Ala Pro Gln Pro Pro Asp Val Gly Ser Ser Asp
            180                 185                 190

Pro Leu Ser Met Val Gly Pro Ser Gln Gly Arg Ser Pro Ser Tyr Ala
        195                 200                 205

Ser

```
<210> SEQ ID NO 14
<211> LENGTH: 146
<212> TYPE: PRT
<213> ORGANISM: Thermotoga maritima
<220> FEATURE:
<221> NAME/KEY: PEPTIDE
<222> LOCATION: (110)..(146)
<223> OTHER INFORMATION: Homo sapiens

<400> SEQUENCE: 14
```

Met Lys Gln Glu Lys Leu Ser Leu His Asp Val Leu Ile Arg Pro Ile
1               5                   10                  15

Ile Thr Glu Lys Ala Leu Ile Leu Arg Glu Gln Arg Lys Tyr Val Phe
            20                  25                  30

Glu Val Asn Pro Leu Ala Asn Lys Asn Leu Val Lys Glu Ala Val Glu
        35                  40                  45

Lys Leu Phe Asn Val Lys Val Glu Lys Val Asn Ile Leu Asn Met Lys
    50                  55                  60

Pro Lys Pro Lys Arg Arg Gly Ile Phe Gly Lys Thr Arg Ser Trp
65                  70                  75                  80

Lys Lys Ala Val Val Thr Leu Lys Glu Gly Tyr Thr Ile Lys Glu Leu
                85                  90                  95

Glu Gly Glu His Ser Ser Ser Ser Asp Asp Asp Asp Lys Lys Cys Asn

```
                    100                 105                 110
Thr Ala Thr Cys Ala Thr Gln Arg Leu Ala Asn Phe Leu Val His Ser
            115                 120                 125

Ser Asn Asn Phe Gly Ala Ile Leu Ser Ser Thr Asn Val Gly Ser Asn
            130                 135             140

Thr Tyr
145

<210> SEQ ID NO 15
<211> LENGTH: 147
<212> TYPE: PRT
<213> ORGANISM: Homo sapiens

<400> SEQUENCE: 15

Met Val Pro Ile Gln Lys Val Gln Asp Asp Thr Lys Thr Leu Ile Lys
1               5                   10                  15

Thr Ile Val Thr Arg Ile Asn Asp Ile Ser His Thr Gln Ser Val Ser
                20                  25                  30

Ser Lys Gln Lys Val Thr Gly Leu Asp Phe Ile Pro Gly Leu His Pro
            35                  40                  45

Ile Leu Thr Leu Ser Lys Met Asp Gln Thr Leu Ala Val Tyr Gln Gln
    50                  55                  60

Ile Leu Thr Ser Met Pro Ser Arg Asn Val Ile Gln Ile Ser Asn Asp
65                  70                  75                  80

Leu Glu Asn Leu Arg Asp Leu Leu His Val Leu Ala Phe Ser Lys Ser
                85                  90                  95

Cys His Leu Pro Trp Ala Ser Gly Leu Glu Thr Leu Asp Ser Leu Gly
            100                 105                 110

Gly Val Leu Glu Ala Ser Gly Tyr Ser Thr Glu Val Val Ala Leu Ser
            115                 120                 125

Arg Leu Gln Gly Ser Leu Gln Asp Met Leu Trp Gln Leu Asp Leu Ser
            130                 135                 140

Pro Gly Cys
145

<210> SEQ ID NO 16
<211> LENGTH: 4
<212> TYPE: PRT
<213> ORGANISM: Artificial
<220> FEATURE:
<223> OTHER INFORMATION: N-terminal extension

<400> SEQUENCE: 16

Met Glu Ala Glu
1
```